United States Patent
Viitanen (10) Patent No.: US 10,101,266 B2
(45) Date of Patent: Oct. 16, 2018

(54) METHOD AND SYSTEM FOR GAS CONCENTRATION MEASUREMENT OF GAS DISSOLVED IN LIQUIDS

(71) Applicant: Vaisala Oyj, Vantaa (FI)

(72) Inventor: Veli-Pekka Viitanen, Helsinki (FI)

(73) Assignee: Vaisala Oyj, Vantaa (FI)

(*) Notice: Subject to any disclaimer, the term of this patent is extended or adjusted under 35 U.S.C. 154(b) by 0 days.

(21) Appl. No.: 15/023,721

(22) PCT Filed: Sep. 17, 2014

(86) PCT No.: PCT/FI2014/050710
§ 371 (c)(1),
(2) Date: Mar. 22, 2016

(87) PCT Pub. No.: WO2015/044516
PCT Pub. Date: Apr. 2, 2015

(65) Prior Publication Data
US 2016/0231229 A1 Aug. 11, 2016

(30) Foreign Application Priority Data
Sep. 24, 2013 (FI) .................................... 20135951

(51) Int. Cl.
*G01N 21/25* (2006.01)
*G01N 21/31* (2006.01)
(Continued)

(52) U.S. Cl.
CPC ............. *G01N 21/255* (2013.01); *G01J 3/26* (2013.01); *G01J 3/42* (2013.01); *G01J 3/427* (2013.01);
(Continued)

(58) Field of Classification Search
CPC ................ G01N 21/255; G01N 21/31; G01N 2201/068; G01N 2201/12715; G01N 2021/3536; G01N 21/274
See application file for complete search history.

(56) References Cited

U.S. PATENT DOCUMENTS 4,500,207 A * 2/1985 Maiden .............. G01N 21/3518
250/343
5,002,391 A * 3/1991 Wolfrum ................ G01N 21/39
250/338.5
(Continued)

FOREIGN PATENT DOCUMENTS

CN 101074940 A 11/2007
CN 101427114 A 5/2009
(Continued)

OTHER PUBLICATIONS

Wang et al: High performance Co"2 measurement based on pressure modulation. Procedia Engineering, Jan. 1, 2010. vol. 5, pp. 1208-1211.

*Primary Examiner* — Sang Nguyen
(74) *Attorney, Agent, or Firm* — Seppo Laine Oy (57) ABSTRACT

The present invention concerns a method and system for gas concentration measurement of gas or gas mixtures dissolved in liquids. A gas or gas mixture dissolved in a liquid sample is extracted from the liquid sample using an extraction system and conducted into a measurement chamber. Then a measurement signal is generated by means of a radiant source and the measurement signal is directed to a measurement object in a measurement chamber containing the gas or gas mixture to be measured. The measurement signal is filtered using at least two wavelengths, whereupon the filtering is preferably implemented by means of an electri-
(Continued)

cally tunable, short-resonator Fabry-Perot interferometer. Then the filtered measurement signals are detected my means of a detector.

23 Claims, 6 Drawing Sheets

(51) Int. Cl.

| | | |
|---|---|---|
| *G01J 3/26* | (2006.01) | |
| *G01J 3/427* | (2006.01) | |
| *G01N 21/3504* | (2014.01) | |
| *G01N 33/28* | (2006.01) | |
| *G01J 3/42* | (2006.01) | |
| *G01N 21/27* | (2006.01) | |

(52) U.S. Cl.
CPC .......... *G01N 21/274* (2013.01); *G01N 21/31* (2013.01); *G01N 21/3504* (2013.01); *G01N 33/2841* (2013.01); *G01N 2021/3536* (2013.01); *G01N 2201/068* (2013.01); *G01N 2201/12715* (2013.01)

(56) References Cited

U.S. PATENT DOCUMENTS

| | | |
|---|---|---|
| 5,400,641 A | 3/1995 | Slemon et al. |
| 6,037,592 A | 3/2000 | Sunshine et al. |
| 6,526,805 B1 | 3/2003 | Babes-Dornea et al. |
| 7,511,819 B2 | 3/2009 | DiFoggio |
| 7,749,436 B2 * | 7/2010 | Mori .................. G01N 21/3504 422/50 |
| 9,046,481 B2 * | 6/2015 | Edler .................... G01J 3/4338 |
| 2002/0194932 A1 * | 12/2002 | Gysling .................... G01F 1/34 73/861.42 |
| 2006/0139646 A1 | 6/2006 | DiFoggio |
| 2007/0013911 A1 | 1/2007 | DiFoggio |
| 2007/0242275 A1 * | 10/2007 | Spartz .................. G01N 21/031 356/451 |
| 2010/0037892 A1 * | 2/2010 | Bartlett .................... B63C 11/32 128/202.12 |
| 2010/0050760 A1 * | 3/2010 | Vannuffelen ........... E21B 49/10 73/152.27 |
| 2010/0223015 A1 * | 9/2010 | Phillips .................... G01J 3/02 702/24 |
| 2011/0109905 A1 | 5/2011 | Martin |
| 2011/0211193 A1 | 9/2011 | Saveliev et al. |
| 2011/0308391 A1 | 12/2011 | Degreeve et al. |
| 2012/0055232 A1 * | 3/2012 | Thorson ............. G01N 21/1702 73/24.02 |
| 2012/0097852 A1 * | 4/2012 | Weckstrom .......... G01N 21/314 250/343 |
| 2014/0241394 A1 * | 8/2014 | Olson ...................... G01N 3/60 374/8 |

FOREIGN PATENT DOCUMENTS

| | | |
|---|---|---|
| CN | 101975761 A | 2/2011 |
| CN | 202141720 U | 2/2012 |
| CN | 103018355 A | 4/2013 |
| EP | 0509249 B1 | 7/2000 |
| EP | 1840557 A1 | 10/2007 |
| EP | 2028341 A1 | 2/2009 |

\* cited by examiner

METHOD AND SYSTEM FOR GAS CONCENTRATION MEASUREMENT OF GAS DISSOLVED IN LIQUIDS

TECHNICAL FIELD OF THE INVENTION

The present invention relates to a method for gas concentration measurement of gas or gas mixtures dissolved in liquids. The invention also relates to a system for gas concentration measurement of gas or gas mixtures dissolved in liquids.

BACKGROUND OF THE INVENTION

Gas concentration is conventionally measured by means of measurement apparatuses based on non-dispersive IR techniques (NDIR). IR absorption multigas analyzers can further measure the absorption of a gas sample at several wavelength bands. Generally frequent calibration of gas analyzers is necessary for precise determination of the concentration of a gas or gas mixture.

EP 1482301 B1 teaches that a non-dispersive infrared (NDIR) gas analyzer is based on the absorption of infrared radiation in a gas sample. A radiation source directs a beam of infrared radiation through a measuring chamber to a radiation detector. The output signal depends on the strength of the absorption of radiation in the gas sample. The optical wavelength band used for the measurement is selected non-dispersively with an optical bandpass filter. The radiation source typically consists of an electrically heated filament and radiation collecting optics. The gas mixture to be analyzed is fed through the measurement chamber, whereupon the gas mixture is contained in the chamber for analysis. The measuring chamber can be a tubular space provided with entrance and exit windows that are transparent at the measurement wavelength and with inlet and outlet for the sample gas. Radiation is absorbed by the gas sample when passing through the measuring chamber.

U.S. Pat. No. 5,646,729 discloses a single-channel gas concentration measurement method and apparatus. According to the method, a radiant source is employed to generate a measuring signal, the measuring signal is subsequently directed to a measurement object containing a gas mixture to be measured, the measuring signal is subsequently bandpass filtered using at least two passband wavelengths, and the filtered measuring signals are detected by a detector. According to the invention, the bandpass filtering step is implemented by a single electrostatically tunable, short-resonator Fabry-Perot interferometer.

U.S. Pat. No. 4,500,207 further describes an apparatus for non-dispersive optical determination of the concentration of an identifiable gas, such as a hydrocarbon, in a mixture such as atmospheric air comprises a sample chamber to contain a sample of the mixture, a source of IR radiation at a wavelength absorbed by the gas beamed through the sample chamber to a detector and transducer means to change the gas pressure within the chamber to determine the change in radiation intensity detected at different pressures.

U.S. Pat. No. 5,077,469 describes a compensation and calibration method for a non-dispersive infrared gas analyzer which includes an infrared source of radiation, a measuring path, a reference path, modulation devices, a detector for differential pressure measuring, comprising the steps of: First and prior to measurement, having a variable basic concentration in the measuring component is forced through the reference branch and through the measuring branch and the detector is set to a zero position. A dual calibration chamber is placed into the two reference paths while both of them are still passed through by the reference gas, one of the calibration chambers including a particular concentration in the measuring gas, the other one lacking that measuring gas. The sensitivity and amplification of the detector that obtains as a result of changes in the radiation on account of placing the calibration chamber into the reference and measuring path is adjusted, whereupon the calibration chamber is removed, reference gas still is passed through the reference chamber, while measuring gas now flows through the measuring chamber.

U.S. Pat. No. 5,850,354 discloses a method and apparatus for calibrating an NDIR gas analyzer. The apparatus under calibration is calibrated with the help of a reference apparatus under controlled conditions. The reference apparatus is a laboratory-calibrated NDIR measurement apparatus in an arrangement based on circulating ambient air via both a measurement chamber of the measurement apparatus under calibration and measurement chamber of the laboratory-calibrated measurement apparatus. Adjusting the reading of a display, or alternatively, an output signal of the measurement apparatus under calibration to be equal to the reading of the display, or the output signal, respectively, of the reference apparatus is performed by a control device of the measurement apparatus.

EP 0600711 A2 teaches that a method for field calibrating a system adapted for spectrographic analysis of gaseous substances uses an easily available gas, for example ambient air, thereby providing for field calibration of the system without the inconvenience of using a purified noble gas and a premeasured calibration gas mixture. During calibration, spectrograms from the easily available gas are generated by the system at various number density levels of the gas. Information from the spectrograms is the used in setting an operating parameter of the system.

U.S. Pat. No. 5,369,278 discloses a calibration method for gas concentration measurement with an NDIR technique based on optical absorption. Radiation is imposed onto the gas mixture under measurement contained in a measurement channel isolated at least partially from its environment, the intensity of radiation transmitted through the gas is measured, the gas concentration is computed from the measured intensity, in order to calibrate the measurement apparatus the gas state variables are deviated in a controlled manner, whereby the level of transmitted radiation intensity is changed, and the intensity of the transmitted radiation is measured in at least two known points of the gas state variables, thus obtaining data for calibration of the measurement apparatus employed. The gas state variables are deviated by heating the gas under measurement in such a short time during which the ambient concentration of the gas undergoes no change, whereby the gas density is decreased with the increasing temperature, while the partial pressure of the gas under measurement stays essentially constant.

U.S. Pat. No. 4,409,814 teaches that there are typically three types of gas extracting devices for extracting gas suspended in the insulating oil, i.e. a Toricelli's vacuum type, a combination of a mercury diffusion pump and Toepler pump type, and a combination of a vacuum pump and a moving valve type of gas extracting device. In the third type, i.e., the vacuum pump and moving valve type of gas extracting device, the interior of a vessel, i.e. a cylinder, is first maintained in a vacuum state by the vacuum pump. After completely extracting the gas into the cylinder, the gas is guided into a gas accumulating tube by operation of the moving valve. The moving valve, i.e., the piston coupled with the cylinder, can only be moved once by switching over the valves associated with and mounted on both sides of the cylinders.

DE 10252652 A1 discloses a device for de-gasification of fluid samples. The suction side of a mercury-free vacuum pump is connected to a de-gasification vessel for the dosed sample. Its pressure side is connected to an expansion vessel for gas collection. The expansion vessel is subsequently connected through one or more valves to the vacuum side of the pump, to extract gas from it. The expansion vessel has a variable volume and a gas extraction facility. A gas sample dosing valve is connected to the expansion system, for a gas analysis unit. Volume increase in the expansion vessel is registered by a bellows, or by a piston-operated gas burette. A pressure sensor registers the vacuum. A valve allows the gas quantity released to be measured with the pressure sensor.

JP 2004-037135 A describes an apparatus and a method for monitoring a dissolved gas in oil. A non bellows type gas extracting chamber is air tightly connected to the inside of the oil equipment via a first pipeline having an oil conveying pump and a second pipeline. An extracted gas accommodation chamber is provided while being separated from the gas extracting chamber, and both the chambers are air tightly connected via an on/off valve. In a gas extraction process, the gas extracting chamber that is filled with oil to be tested is allowed to communicate with the extracted-gas accommodation chamber that is kept vacuum by opening the on/off valve, the on/off valve is closed for cutting off both the chambers after gas is extracted and the oil to be tested is sent back into the oil equipment without coming into contact with the air. The extracted gas inside the extracted gas accommodation chamber is mixed with the air and is analyzed by a gas analyzer.

SUMMARY OF THE INVENTION

NDIR spectrometers are versatile tools for gas analysis. Single-channel gas concentration measurement methods and apparatuses featuring micromachined, electrically tunable Fabry-Perot Interferometer (FPI) filters for built-in reference measurement known from prior art cannot be used for direct analysis of gases dissolved in liquids due to high IR absorption by the liquids as well as due to changes in the molecular spectra.

The embodiments of the present invention are based on the object to provide a method and a system for gas concentration measurement of gas or gas mixtures dissolved in liquids. The embodiments of the system should ensure operation without calibration intervention. The embodiments of the invention are in particular useful for gas concentration measurement of gas or gas mixtures dissolved in crude oil, transformer oil, mineral oil products or chemical products.

These and other objects are achieved by the embodiments of the present invention, as hereinafter described and claimed. According to an aspect of the invention, there is provided a method for gas concentration measurement comprising the steps of:

a gas or gas mixture dissolved in a liquid sample is extracted from the liquid sample using an extraction system and conducted into a measurement chamber,
a measurement signal is generated by means of a radiant source,
the measurement signal is directed to a measurement object in the measurement chamber containing the gas or gas mixture to be measured,
the measurement signal is modified by a filter or a wavelength dispersive element in order to enable the observation of the wavelength dependence of the signal intensity, and
the modified signal is detected by means of a detector (8) or a detector matrix.

In an embodiment, the filtering of the measurement signal is implemented by means of an electrically tunable, short-resonator Fabry-Perot interferometer or the wavelength dispersion of the measurement signal is implemented by means of a grating.

In another embodiment, the wavelength range includes the absorption maximum and the absorption minimum. In an embodiment, the wavelength range contains easily measurable variations in the absorption strength.

According to an embodiment, the signal intensity as a function of the wavelength is measured at an optimal wavelength range at a first pressure $P_1$, then the pressure is varied to a second pressure $P_2$, and then the signal intensity as a function of the wavelength $\lambda$ is measured at the said optimal wavelength range at the second pressure $P_2$.

In an embodiment, the pressure variation is realized by moving a bellows piston connected to the measurement chamber or using a liquid pump capable of generating a pressure difference of approximately 1 [bar] or more, combined with a vacuum-tight liquid vessel.

In another embodiment, the gas or gas mixture to be measured is dissolved in crude oil, transformer oil, a mineral oil product or a chemical product.

According to another aspect of the invention, the object of embodiments can be also achieved by a system for gas concentration measurement comprising:

at least one extraction system for extraction of a gas or gas mixture dissolved in a liquid sample,
at least one radiant source for generating a measurement signal,
at least one measurement chamber with an optical path,
a measurement object containing the gas or gas mixture to be measured,
at least one electrically tunable, short-resonator Fabry-Perot interferometer or a grating,
at least one detector or detector matrix suited for detecting said filtered or wavelength-dispersed measurement signals, and
at least one pressure sensor for measuring pressure in the measurement chamber.

In an embodiment, the extraction system for extraction of the gas or gas mixture dissolved in the liquid sample comprises a bellows piston for fluid sampling, gas extraction by vacuum and subsequent gas compression, and a linear motor for operation of the bellows piston.

In another embodiment, the radiant source is an electrically modulatable radiant source.

According to an embodiment, the bellows piston is connected to at least one fluid inlet pipe with at least one fluid valve and to at least one fluid outlet pipe with at least one fluid valve.

According to another embodiment, the bellows piston is connected to at least one gas pipe which is connected to the measurement chamber. The gas pipe preferably comprises at least one gas valve. The bellows piston can be replaced by a liquid pump capable of generating a pressure difference of approximately 1 [bar] or more, combined with a vacuum-tight liquid vessel.

In an embodiment, the extraction system can reach pressure levels below 1 [mbar].

In another embodiment, the at least one electrically tunable, short-resonator Fabry-Perot interferometer is arranged between the radiant source and the measurement chamber or between the measurement chamber and the detector.

According to an embodiment, the system is including at least one electronic device such as a computer for zero signal generation by mathematical extrapolation of the first signal intensity measured as a function of the wavelength at at least two wavelengths at a first pressure and the second signal intensity measured as a function of the wavelength at at least two wavelengths at a second pressure to zero pressure and/or for subtraction of the offset of the zero signal intensity from the offsets of the first signal intensity and the second signal intensity.

In an embodiment, the system is including at least one electronic device such as a computer for controlling the extraction system as a function of pressure in the measurement chamber and/or for controlling at least one liquid valve and/or at least one gas valve.

In another embodiment, the system is including at least one electronic device such as a computer with at least one memory for storing measurement data such as name or number of the liquid sample to be measured, mass flow of the liquid sample, temperature of the liquid sample, volume of the liquid sample, pressure in the measurement chamber, pressure in the bellows piston, pressure at least one liquid valve, pressure at least one gas valve, first pressure $P_1$, second pressure $P_2$, zero pressure $P_0$, intensity data as a function of wavelength, radiant source data, Fabry-Perot interferometer data, detector data, and/or signals as a function of wavelengths. Preferably the system is furthermore including a computer-aided algorithm.

According to an embodiment, the system is including a liquid pump capable of generating a pressure difference of approximately 1 [bar] or more, combined with a vacuum-tight liquid vessel.

Considerable advantages are obtained by means of the present invention. Gas concentration measurement methods and apparatuses featuring micromachined, electrically tunable Fabry-Perot Interferometer (FPI) filters for built-in reference measurement can be used for analysis of gases or gas mixtures dissolved in liquids. In particular a gas concentration of a gas or gas mixture dissolved in crude oil, transformer oil, a mineral oil product or a chemical product can be measured. Especially, the invention improves the accuracy of measuring very small amounts typically parts per million by volume of gas in crude oil, transformer oil, mineral oil products or chemical products. The present invention can provide accurate results also when the shape of the emission spectrum changes.

Long service intervals of a system according to the present invention can be considered as advantageous over systems currently on the market. For example in high voltage asset condition monitoring a dissolved gas IR analyzer according to the present invention does not require intervention like manual calibration. Due to the autocalibration the dissolved gas IR analyzer can operate several years without any intervention. Frequent calibration of the IR gas analyzer is not necessary for precise determination of the concentration of a gas or gas mixture to be measured. The life of the interferometer construction is practically unlimited. Gas or gas mixtures can be completely extracted from the liquid sample for measurement and measurements are physically stable. The production, installation and maintenance of a system according to the present invention can be furthermore considered as not cost-intensive.

BRIEF DESCRIPTION OF THE DRAWINGS

For a more complete understanding of particular embodiments of the present invention and their advantages, reference is now made to the following descriptions, taken in conjunction with the accompanying drawings. In the drawings.

DETAILED DESCRIPTION OF EMBODIMENTS OF THE INVENTION

Figure 1:
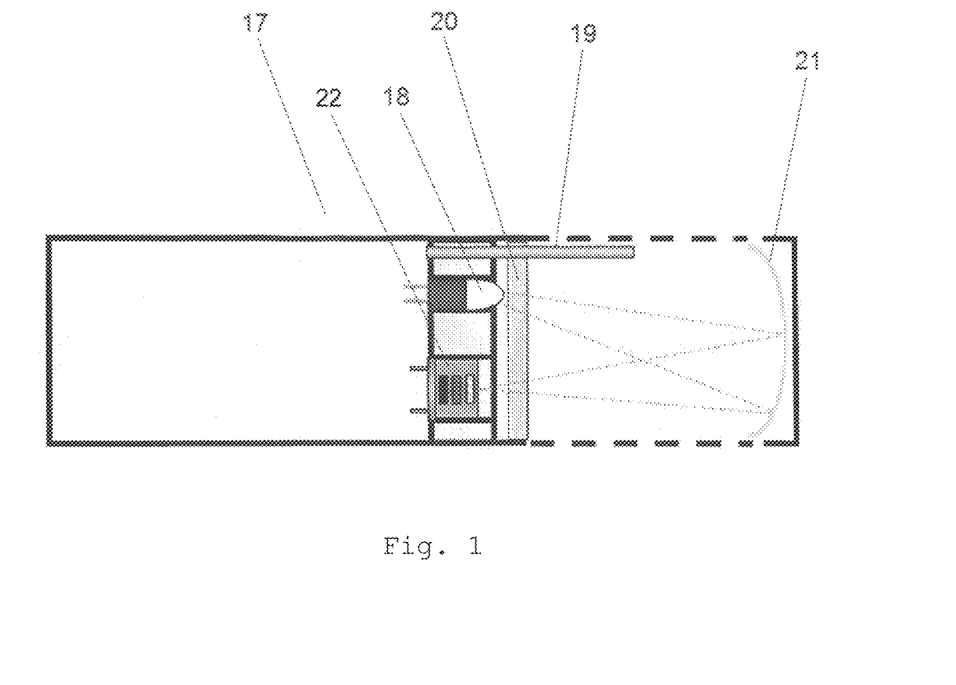
FIG. 1 illustrates a schematic view of a non-dispersive infrared gas analyzer.

In FIG. 1 a schematic view of a common NDIR gas analyzer 17 is illustrated. Light is emitted from a miniature filament lamp 18, passed through a heated sapphire window 20, reflected by a heated gold plated mirror 21 and detected by a FPI detector 22. The NDIR gas analyzer 17 may include a temperature sensor 19. The NDIR gas analyzer 17 further features an electrically tunable Fabry-Perot interferometer located in front of the FPI detector 22. In addition to measuring absorption, the micromechanical Fabry-Perot interferometer enables a reference measurement at a wavelength $\lambda_2$ where no absorption occurs. When taking the reference measurement, the Fabry-Perot interferometer is electrically adjusted to switch the bypass band from the absorption wavelength $\lambda_1$ to a non-absorption wavelength $\lambda_2$. The reference measurement compensates for any potential changes in the light source intensity as well as for contamination and dirt accumulation in the optical path as long as the shape of the spectrum does not change.

Figure 2:
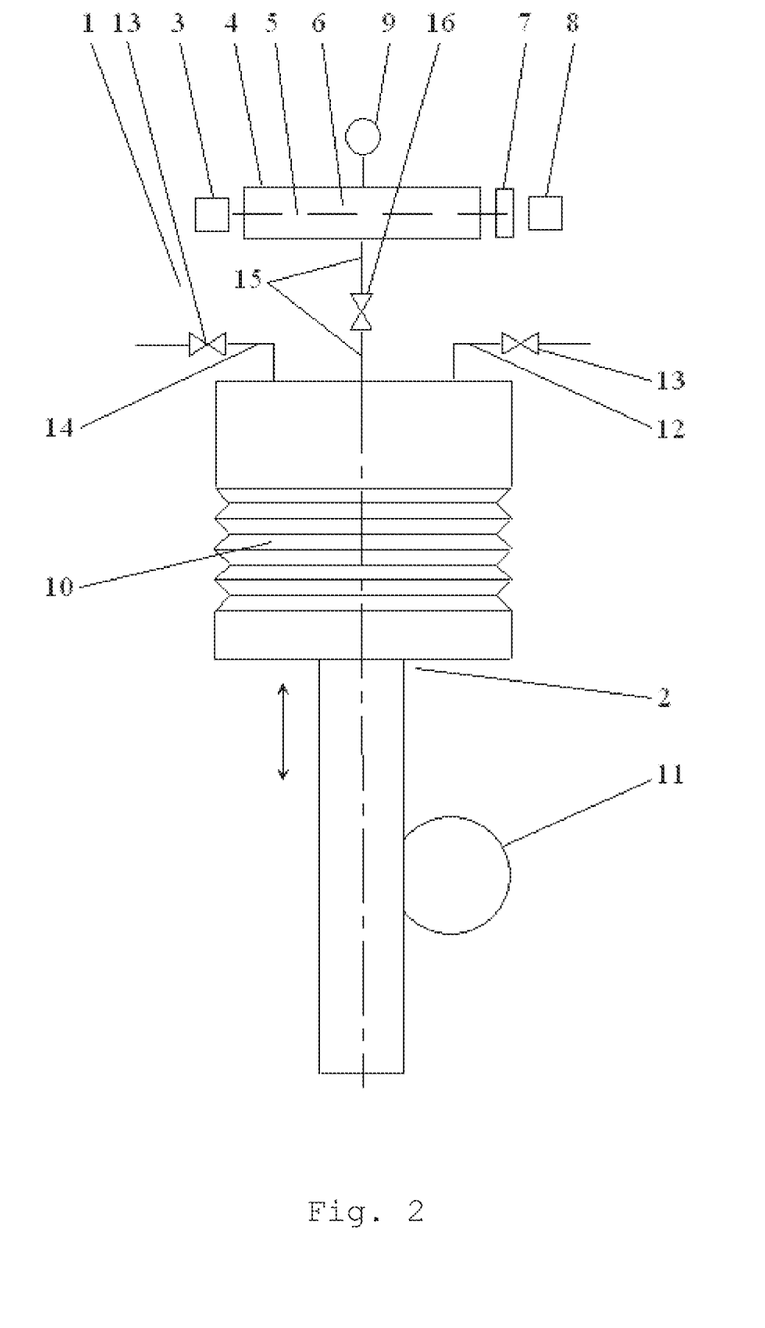
FIG. 2 illustrates a schematic view of a system for gas concentration measurement according to a first embodiment of the present invention.

In FIG. 2 a schematic view of a system for gas concentration measurement 1 according to a first embodiment of the present invention is shown. A liquid such as crude oil, transformer oil, a mineral oil product or a chemical product may be piped through a pipe 12 into a bellows piston 10 for liquid sampling. After closing the at least one liquid valve 13, a gas or a gas mixture is extracted from the liquid sample by vacuum advantageously combined with agitation of the liquid and subsequently the gas or gas mixture is compressed using a linear motor 11 for operation of the bellows piston 10. The bellows piston 10 is connected to at least one gas pipe 15 which is connected to the measurement chamber 4. The at least one gas pipe 15 comprises at least one gas valve 16. After opening the at least one gas valve 16, the gas or gas mixture can flow into the measurement chamber 4, which is equipped with at least one pressure sensor 9. With the help of the extraction system 2, a number of accurate pressure levels can be generated in the measurement system 2. The at least one gas valve may be closed to hold the pressure stable in the measurement chamber 4.

Then a measurement signal may be generated by means of a radiant source 3. The measurement signal may be directed to a measurement object 6 in the measurement chamber 4 containing the gas or gas mixture to be measured. The measurement signal may be bandpass filtered using at least two passband wavelengths $\lambda_1$, $\lambda_2$, whereupon the bandpass filtering may be implemented by means of a electrically tunable, short-resonator Fabry-Perot interferometer 7. The measurement signal may be also wavelength-dispersed by means of a grating. Then the filtered or wavelength-dispersed measurement signals are detected by means of a detector 8.

According to a certain embodiment, the wavelength range includes the absorption maximum and the absorption minimum. According to a certain other embodiment, the wavelength range contains easily measurable variations in the absorption strength. In other words, a first wavelength $\lambda_1$ may be at the absorption maximum and a second wavelength $\lambda_2$ may be at minimum absorption. A wavelength $\lambda$ may further be between the absorption maximum and the absorption minimum. After measuring the signal $S_1$ as a function of the wavelength at pressure $P_1$, e.g. at the at least two wavelengths $\lambda_1$ and $\lambda_2$, the pressure $P_1$ may be varied to pressure $P_2$. Then signal measurements at pressure $P_2$ or at several different pressures may be performed. Then the signal $S_0$ may be generated by mathematical extrapolation the signal to zero pressure $P_0$=[0 bar], and then the offset $S_0$ is subtracted from the signals $S_1$ and $S_2$.

The intensity I of radiation incident on the detector is dependent on the absorption in the measurement channel according to the Lambert-Beer's law $$I = I_0 e^{-\sigma L N}$$

where $I_0$ is the intensity of radiation incident on the detector, $\sigma(\lambda)$ is the gas absorption cross section, N is the gas number density and L is the length of the optical path. The equation can be also written as $$N = -\frac{1}{\sigma(\lambda) L} \ln\left(\frac{I}{I_0}\right).$$

If the absorption is small, e.g. $I/I_0 > 0.95$, the concentration can be estimated by $$N = \frac{1}{\sigma(\lambda) L}\left(1 - \frac{I}{I_0}\right).$$

In this case the maximum error of concentration approximation would remain below 2.5 [%]. In this simplified example case where the concentration can be approximated by a linear function of the ratio of absorption and reference signals, the zero concentration signal can be found by repeating the measurement after varying the pressure of the measured gas. The ratio of the absorption and reference signals S is $$S = \left(\frac{I}{I_0}\right)_{hence}$$
$$S(P0) = S(P2) - \frac{S(P1) - S(P2)}{(P1 - P2)} * (P2 - P0).$$

Finding $S_0(P_0)$ is essential for the long term stability of the measurement. The conventional principle of using the ratio of the absorption signal measured at a first wavelength and reference signal measured at a second wavelength excludes all sources of error that affect the both channels in a similar way, e.g. changes in amplifier gain or dust on optical surfaces. However, a wavelength-dependent change in the light source emission spectrum of the optical elements can easily induce an offset-type error in the signal, since $I/I_0$ will not equal 1 or any constant value at zero absorption. The present invention can provide accurate results also when the shape of the emission spectrum changes.

With the help of a gas extraction system 2, equipped with a pressure sensor 9, it is very easy to generate a number of accurate pressure levels, hold the pressure stable, and perform signal measurements at several different pressures. The number of pressure levels can naturally be higher than 2. This would also help to compensate for errors caused by signal nonlinearity in the offset correction.

Figure 3:
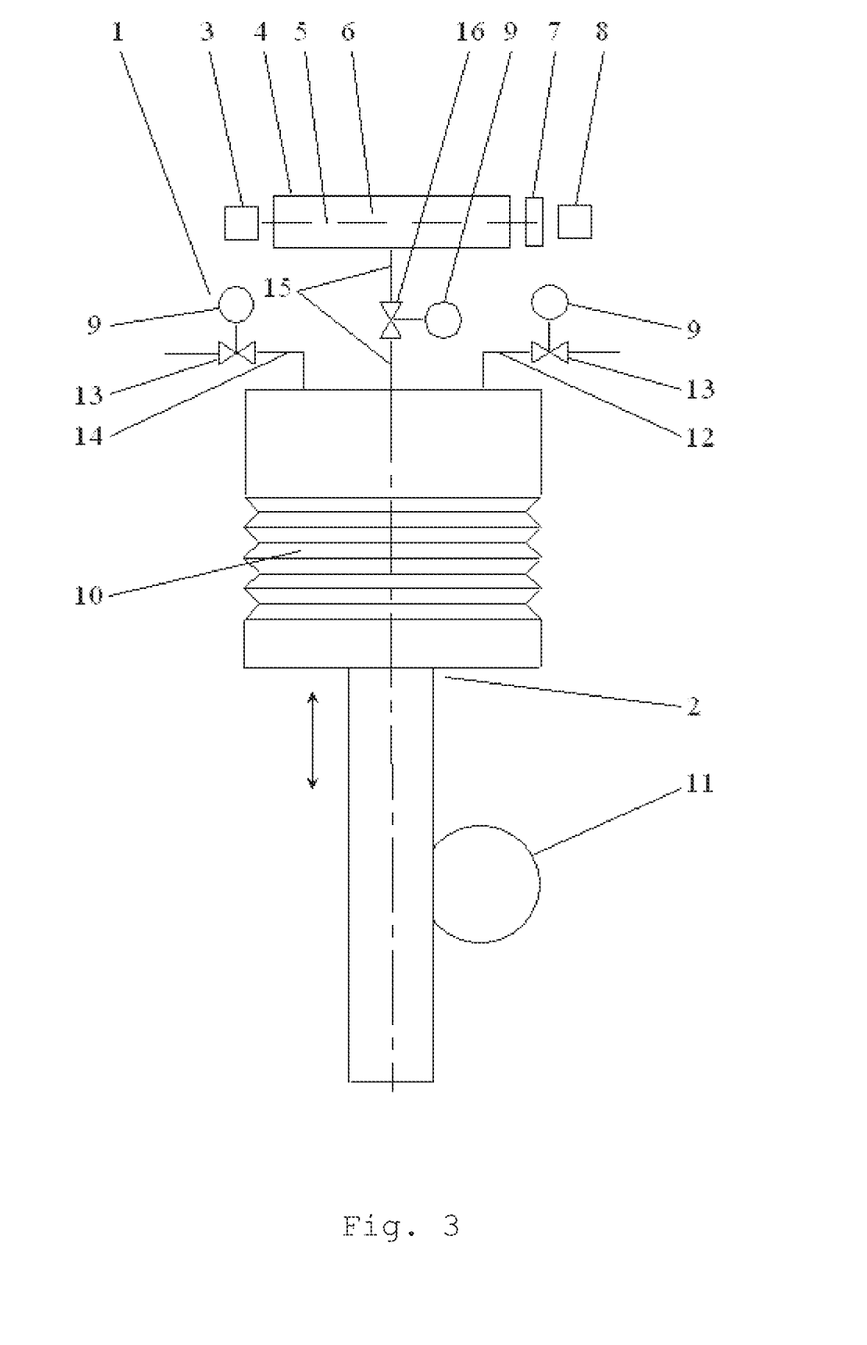
FIG. 3 illustrates a schematic view of a system for gas concentration measurement according to a second embodiment of the present invention.

In FIG. 3 a schematic view of a system for gas concentration measurement 1 according to a second embodiment of the present invention is shown. A liquid such as crude oil, transformer oil, a mineral oil product or a chemical product may be piped through a pipe 12 into a bellows piston 10 for liquid sampling. After closing the at least one liquid valve 13, a gas or a gas mixture is extracted from the liquid sample by vacuum advantageously combined with agitation of the liquid and subsequently the gas or gas mixture is compressed using a linear motor 11 for operation of the bellows piston 10. The bellows piston 10 is connected to at least one gas pipe 15 which is connected to the measurement chamber 4. The at least one gas pipe 15 comprises at least one gas valve 16. Pressure sensors 9 are arranged at the liquid valves 13 and at the gas valve 16. The measurement chamber 4 may be equipped with at least one further pressure sensor 9, which is not shown in FIG. 3. A valve may also be arranged at the bellows piston 10. After opening the at least one gas valve 16, the gas or gas mixture can flow into the measurement chamber 4. With the help of the extraction system 2 or liquid pump capable of generating a pressure difference of approximately 1 [bar] or more, combined with a vacuum-tight liquid vessel, a number of accurate pressure levels can be generated. The at least one gas valve may be closed to hold the pressure stable in the measurement chamber 4. The system may include at least one electronic device such as a computer for zero signal $S_0$ generation by mathematical extrapolation of the first and second signal $S_1$, $S_2$ to zero pressure $P_0$ and/or for subtraction of the offset of the zero signal $S_0$ from the offsets of the first and second signal $S_1$, $S_2$. The system may also include an electronic device such as a computer for controlling the extraction system 2 as a function of pressure in the measurement chamber 4 and/or for controlling at least one liquid valve 13 and/or at least one gas valve 16. The system may further include an electronic device such as a computer with at least one memory for storing measurement data such as name or number of the liquid sample to be measured, mass flow of the liquid sample, temperature of the liquid sample, volume of the liquid sample, pressure in the measurement chamber 4, pressure in the bellows piston 10, pressure at at least one liquid valve 13, pressure at at least one gas valve 16, first pressure $P_1$, second pressure $P_2$, zero pressure $P_0$, intensity data as a function of wavelength, radiant source data, Fabry-Perot interferometer 7 data, detector 8 data, and/or signals $S_1$, $S_2$, $S_0$.

Figure 4:
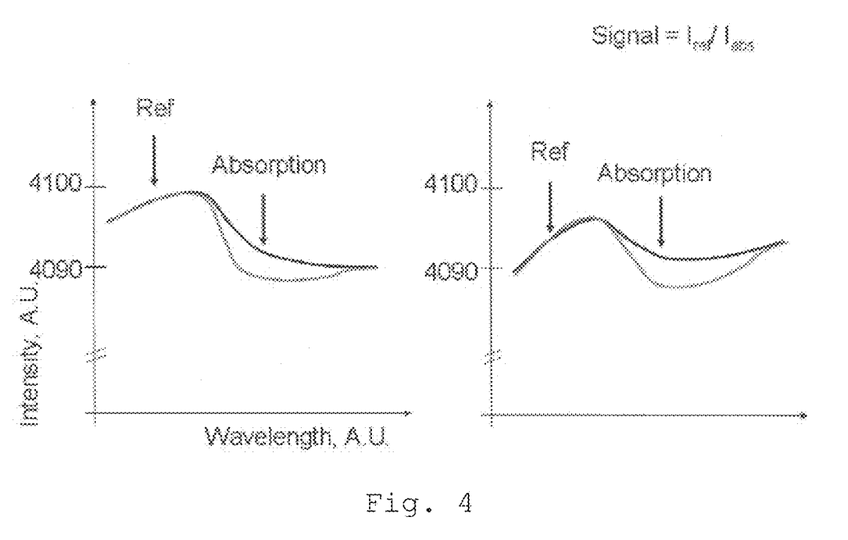
FIG. 4 illustrates two Intensity-Wavelength-Diagrams.

In FIG. 4 two Intensity-Wavelength-Diagrams are illustrated. For different wavelengths reference intensity values $I_{ref}$ and absorption intensity values $I_{abs}$ are shown in both diagrams. According to the present invention the IR radiation passes through the gas sample in the measurement channel and the ratio of IR intensities at at least two wavelengths can be observed, e.g. one wavelength $\lambda_2$ where measured gas has a low IR absorption, and another wavelength $\lambda_1$ where the absorption is at a local maximum. After measuring the intensity as a function of wavelength at the at least two wavelengths $\lambda_1$, $\lambda_2$ at pressure $P_1$, the pressure $P_1$ may be varied to pressure $P_2$. Then signal measurements at pressure $P_2$ or at several different pressures may be performed. Each different pressure level leads to another Intensity-Wavelength-Diagram.

Figure 5:
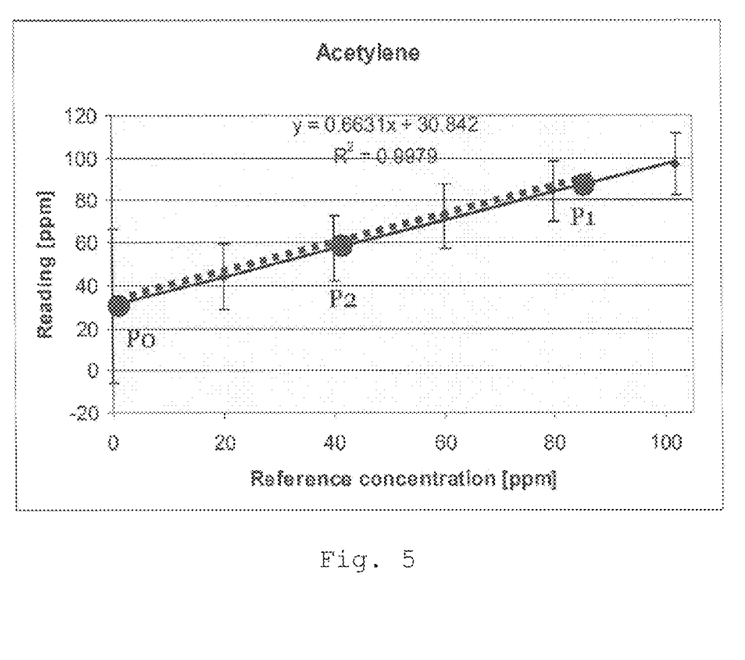
FIG. 5 illustrates an acetylene concentration diagram.

In FIG. 5 an acetylene concentration diagram is shown. After measuring the signal intensity as a function of wavelength at the at least two wavelengths $\lambda_1$, $\lambda_2$ at pressure $P_1$ and varying the pressure $P_1$ to pressure $P_2$, the signal measurements at pressure $P_2$ or at several different pressures may be performed. Then the signal $S_0$ may be generated by mathematical extrapolation the signal to pressure $P_0=0$ [bar].

Figure 6:
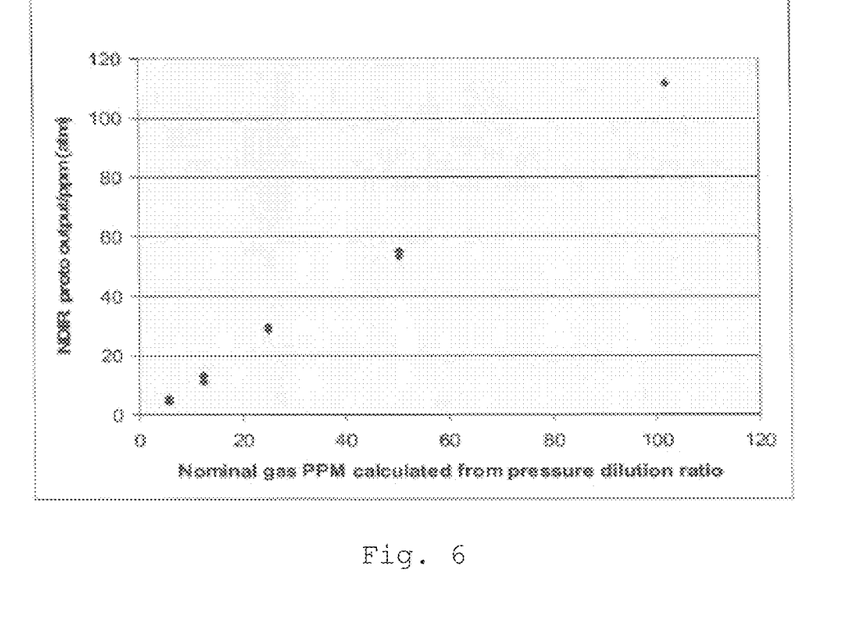
FIG. 6 illustrates an acetylene concentration diagram of measurements where autocalibration and pressure compensation are constant in use.

In FIG. 6 an acetylene concentration diagram of measurements where autocalibration and pressure compensation are constant in use is shown. Nominal gas PPM is calculated from pressure dilution ratio, wherein the offset $S_0$ is subtracted from the offsets of the signals $S_1$ and $S_2$. The desired offset $S(P_1)-S(P_0)$ may also be determined by the approximation $S(P_1)-S(P_0)=(S(P_1)-S(P_2))*(P_1-P_0)/(P_1-P_2)$. Mathematical extrapolation of the signal to zero pressure for generation of the signal $S_0$ is not mandatory for calculation of nominal gas PPM.

Although the present invention has been described in detail for the purpose of illustration, various changes and modifications can be made within the scope of the claims. In addition, it is to be understood that the present disclosure contemplates that, to the extent possible, one or more features of any embodiment may be combined with one or more features of any other embodiment.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

The measurement signal is typically infrared radiation. The invention is in particular not limited to infrared radiation.

LIST OF REFERENCE NUMBERS 1 gas concentration measurement system
2 extraction system
3 radiant source
4 measurement chamber
5 optical path
6 measurement object
7 Fabry-Perot interferometer
8 detector
9 pressure sensor
10 bellows piston
11 linear motor
12 liquid inlet pipe
13 liquid valve
14 liquid outlet pipe
15 gas pipe
16 gas valve
17 NDIR gas analyzer
18 miniature filament lamp
19 temperature sensor
20 sapphire window
21 mirror
22 FPI detector
I intensity
L length of the optical path
N gas number density
$P_0$ zero pressure
$P_1$ first pressure
$P_2$ second pressure
$S_0$ zero signal
$S_1$ first signal
$S_2$ second signal
$\lambda$ wavelength
$\lambda_1$ first wavelength
$\lambda_2$ second wavelength
$\sigma(\lambda)$ gas absorption cross section

The invention claimed is:

1. A method for gas concentration measurement, the method comprising:
   extracting a gas or gas mixture dissolved in a liquid sample using an extraction system and conducted into a measurement chamber,
   generating a measurement signal by a radiant source,
   directing the measurement signal to a measurement object in the measurement chamber containing the gas or gas mixture to be measured,
   modifying the measurement signal by a filter or a wavelength dispersive element in order to enable the observation of the wavelength dependence of the signal intensity, and
   detecting the modified signal by a detector or a detector matrix,
   measuring the signal intensity as a function of the wavelength at at least two wavelengths at a first pressure in the measurement chamber,
   varying a pressure of the gas or gas mixture in the measurement chamber by a bellows piston or a liquid pump, and
   measuring the signal intensity as a function of the wavelength at at least two wavelengths at a second pressure in the measurement chamber.

2. The method according to claim 1, wherein the filtering of the measurement signals is implemented by an electrically tunable, short-resonator Fabry-Perot interferometer or the wavelength dispersion of the measurement signals is implemented by a grating.

3. The method according to claim 1, wherein the wavelength range contains the absorption maximum.

4. The method according to claim 1, wherein the wavelength range contains the minimum absorption.

5. The method according to claim 1, wherein a first wavelength is between an absorption maximum and an absorption minimum, and/or a second wavelength is between an absorption maximum and an absorption minimum.

6. The method according to claim 1, wherein
   a zero signal intensity is determined by mathematically extrapolating the measured signal intensities to zero pressure, and
   an offset of the zero signal intensity is subtracted from offsets of the measured signal intensities.

7. The method according to claim 1, wherein the bellows piston or liquid pump is capable of generating a pressure difference of approximately 1 [bar] or more, combined with a vacuum-tight liquid vessel.

8. The method according to claim 1, wherein the gas or gas mixture is dissolved in crude oil, transformer oil, a mineral oil product or a chemical product.

9. A system for gas concentration measurement, the system comprising:
- at least one extraction system for extraction of a gas or gas mixture dissolved in a liquid sample,
- at least one radiant source for generating a measurement signal,
- at least one measurement chamber with an optical path,
- a measurement object containing the gas or gas mixture to be measured,
- at least one electrically tunable, short-resonator Fabry-Perot interferometer or a grating,
- at least one detector or detector matrix suited for detecting said filtered or wavelength-dispersed measurement signals,
- at least one pressure sensor for measuring pressure in the measurement chamber, and
- a bellows piston or a liquid pump configured to vary a pressure in the measurement chamber, wherein
- the system is configured to measure the signal intensity as a function of the wavelength at at least two wavelengths at a first pressure, and
- the system is configured to measure the signal intensity as a function of the wavelength at at least two wavelengths at a second pressure.

10. The system according to claim 9, wherein the extraction system for extraction of the gas or gas mixture dissolved in the liquid sample further comprises:
a linear motor for operation of the bellows piston.

11. The system according to claim 9, wherein the radiant source is an electrically modulatable radiant source.

12. The system according to claim 9, wherein the bellows piston is connected to at least one liquid inlet pipe with at least one liquid valve.

13. The system according to claim 9, wherein the bellows piston is connected to at least one liquid outlet pipe with at least one liquid valve.

14. The system according to claim 9, wherein the bellows piston is connected to at least one gas pipe which is connected to the measurement chamber.

15. The system according to claim 14, wherein the gas pipe comprises at least one gas valve.

16. The system according to claim 9, wherein the extraction system can reach pressure levels below 1 [mbar].

17. The system according to claim 9, wherein the at least one electrically tunable, short-resonator Fabry-Perot interferometer is arranged between the radiant source and the measurement chamber or between the measurement chamber and the detector.

18. The system according to claim 9, the system including at least one electronic device for zero signal intensity generation by mathematical extrapolation of the first signal intensity measured as a function of the wavelength at at least two wavelengths at a first pressure, and the second signal intensity measured as a function of the wavelength at at least two wavelengths at a second pressure to zero pressure, and/or for subtraction of the offset of the zero signal intensity from the offsets of the first signal intensity and the second signal intensity.

19. The system according to claim 9, the system further comprising an electronic device such as a computer for controlling the extraction system as a function of pressure in the measurement chamber and/or for controlling at least one liquid valve and/or at least one gas valve.

20. The system according to claim 9, the system further comprising an electronic device with at least one memory for storing measurement data, mass flow of the liquid sample, temperature of the liquid sample, volume of the liquid sample, pressure in the measurement chamber, pressure in the bellows piston, pressure at at least one liquid valve, pressure at at least one gas valve, first pressure, second pressure, zero pressure, passband wavelengths, radiant source data, Fabry-Perot interferometer data, detector data, and/or signal intensities as a function of wavelength.

21. The system according to claim 9, the system further comprising a computer-aided algorithm.

22. The system according to claim 9, the system including a liquid pump capable of generating a pressure difference of approximately 1 [bar] or more, combined with a vacuum-tight liquid vessel.

23. A system for gas concentration measurement, the system comprising:
- an extraction system for extracting a gas or gas mixture dissolved in a liquid sample from the liquid sample and a conduction system for conducting the gas or gas mixture into a measurement chamber,
- a radiant source for generating a measurement signal,
- a measurement signal directed to a measurement object in the measurement chamber containing the gas or gas mixture to be measured,
- a filter or a wavelength dispersive element for modifying the measurement in order to enable the observation of the wavelength dependence of the signal intensity,
- a detector or a detector matrix for detecting the modified signal, and
- a bellows piston or a liquid pump configured to vary a pressure in the measurement chamber, wherein
- the system is configured to measure the signal intensity as a function of the wavelength at at least two wavelengths at a first pressure,
- the system is configured to vary the pressure to a second pressure, and
- the system is configured to measure the signal intensity as a function of the wavelength at at least two wavelengths at the second pressure.

* * * * *